US008829183B1

(12) United States Patent
Shelnutt et al.

(10) Patent No.: US 8,829,183 B1
(45) Date of Patent: Sep. 9, 2014

(54) METHOD FOR FORMING COOPERATIVE BINARY IONIC SOLIDS

(71) Applicant: Sandia Corporation, Albuquerque, NM (US)

(72) Inventors: John A. Shelnutt, Tijeras, NM (US); Kathleen E. Martin, Tijeras, NM (US); Zhongchun Wang, Sunnyvale, CA (US); Craig J. Medforth, Oporto (PT)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/758,469

(22) Filed: Feb. 4, 2013

Related U.S. Application Data

(62) Division of application No. 12/756,744, filed on Apr. 8, 2010, now Pat. No. 8,389,715.

(51) Int. Cl.
*C07B 47/00* (2006.01)
*C07D 487/22* (2006.01)

(52) U.S. Cl.
USPC ......................................................... 540/145

(58) Field of Classification Search
USPC ............................................................ 540/145
See application file for complete search history.

(56) References Cited

PUBLICATIONS

Craig John Medforth, et al.; Self-assembled Porphyrin Nanostructures; The Royal Societ of Chemistry 2009; Chem. Commun., 2009, pp. 7261-7277.

*Primary Examiner* — Paul V. Ward
(74) *Attorney, Agent, or Firm* — Daniel J. Jenkins

(57) ABSTRACT

A nanostructured molecular unit and method for forming is described where a cationic porphyrin having an ethanolic substituent species and a metal in the porphyrin cavity is combined with an anionic porphyrin having a sulfonate substituent species and a metal in the porphyrin cavity to form by self-assembly a nanostructured molecular unit with a morphology comprising four dendritic elements connected at a central node.

9 Claims, 8 Drawing Sheets

METHOD FOR FORMING COOPERATIVE BINARY IONIC SOLIDS

CROSS-REFERENCE TO RELATED APPLICATIONS

This application is a divisional application of U.S. Ser. No. 12/756,744 filed Apr. 8, 2010, title "Method for Forming Cooperative Binary Solids", which is incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

BACKGROUND OF THE INVENTION

The present invention relates to self-assembly of organic molecules and, more particularly, to self-assembly of a cationic porphyrin and an anionic porphyrin to form a clover-like biomorphic structure.

Nanostructures self-assembled from organic molecules are of great interest because of their potential applications in areas such as organic photovoltaics and electronics, sensors, nonlinear optics, and catalysis. These nanostructures also offer opportunities for mimicking the processes that occur in biological photosynthesis to produce fuels, and this is especially true when the organic molecular subunits of the nanostructures are porphyrins. Herein, we describe some extraordinary porphyrin biomorphs (biomorphs are structures that are shaped like living organisms) obtained by the self-assembly of two oppositely charged porphyrin ions (tectons). Significantly, the overall shape and size of these biomorphs appears to be largely independent of the metal complexed to the porphyrin. As the metal-centered interactions determine the electronic characteristics of the porphyrin macrocycle (e.g., electron donor versus acceptor), simply altering the metals in the porphyrin tectons provides a high degree of control over the cooperative interactions between the tectons (e.g., charge transfer) and thus the functionality of the organic solid (e.g., charge separation and migration).

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

One embodiment of the present invention is a molecular unit comprising one cationic porphyrin, said cationic porphyrin comprising ethanolic substituent species, and one anionic porphyrin, said anionic porphyrin comprising sulfonate substituent species. When the cationic porphyrin and anionic porphyrin are combined by self-assembly at concentrations greater than approximately 10 micromolar, the molecular units grow to form a nanostructure with a morphology comprising four dendritic elements connected at a central node. The molecular units are considered to be nanostructures because at least one important element of the structure (such as the structures porphyrin cavity or the fine structure of the materials surface) is approximately less than one micron in some dimension although the overall structure can be over one micron in size.

The self-assembled porphyrin structures described herein are unusual because of their elaborate dendritic morphologies and because they provide examples of self-assembled organic materials where the shape and size of the structure is largely independent of the electron donor or acceptor nature of the constituent molecules and the constituent porphyrins are in a one-to-one or nearly one-to-one ratio. This class of organic materials is referred to as Cooperative Binary Ionic (CBI) solids. Such materials can be of interest for solar energy and other applications, as they provide exciting possibilities for varying important photophysical and electronic properties, as well as the possibility of emergent properties with currently unforeseen applications. Other CBI materials self-assembled from donor and acceptor porphyrins or other combinations of cooperative functionality (e.g., light-harvesting porphyrins and catalytic porphyrins) have recently been prepared in our laboratories.

Figure 1:
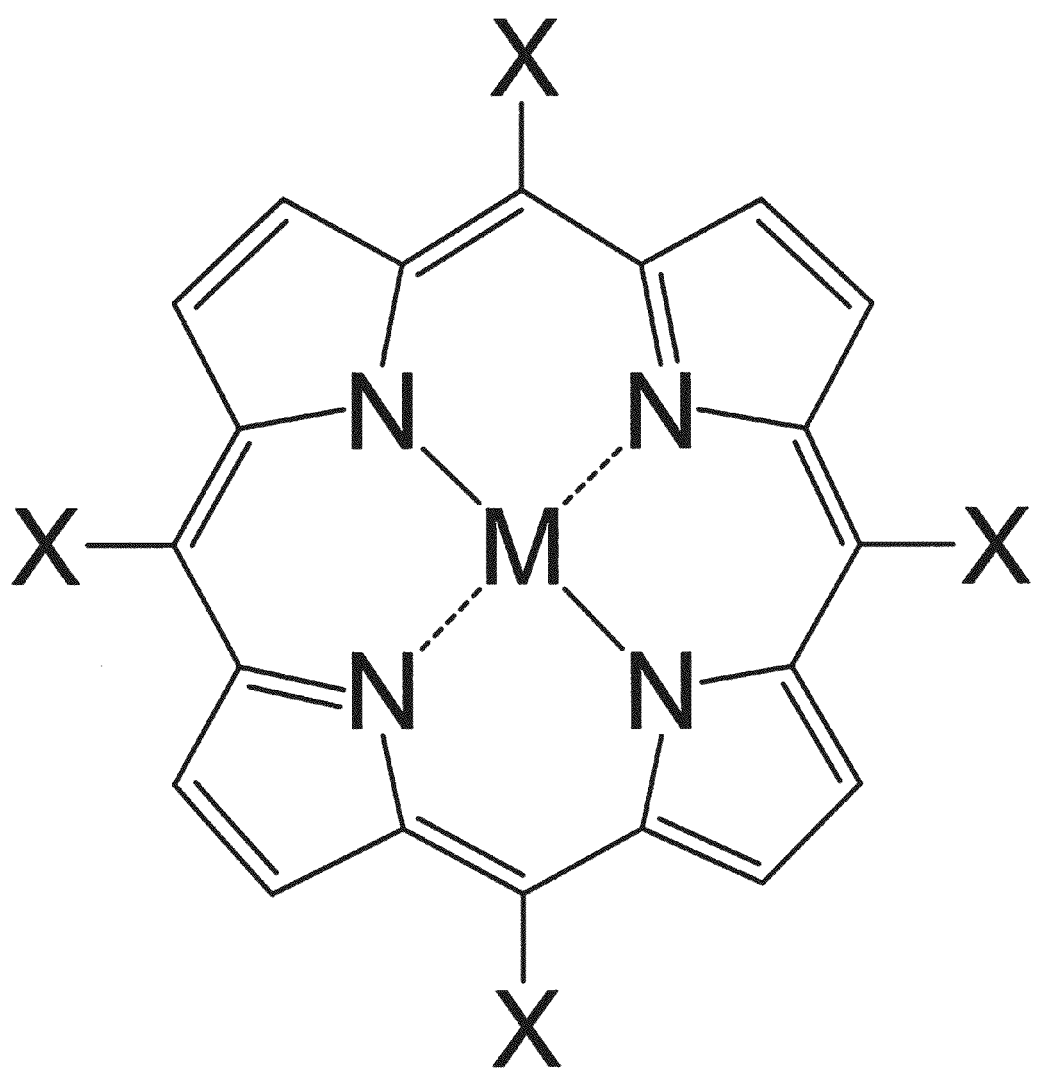
FIG. 1 shows a generic tetrakis 5,10,15,20-substituted porphyrin structure with a substituent species X in each of the four substituent group locations and with a metal M in the porphyrin cavity.

FIG. 1 shows a generic tetrakis 5,10,15,20-substituted porphyrin structure with a substituent species X in each of the four substituent species (group) locations and with a metal M in the porphyrin cavity. In one embodiment, shown in FIG. 2, the cationic porphyrin is zinc(II) tetrakis(N-ethanol-4-pyridinium)porphyrin, where the ethanolic substituent species is N-ethanol-4-pyridinium, and the anionic porphyrin is tin(IV) tetrakis(4-sulfonatophenyl)porphyrin, where the sulfonate substituent species is sulfonatophenyl.

The cationic porphyrin comprises a metal selected from the group Sn, Zn, Co, Mn and Fe. The anionic porphyrin comprises a metal selected from the group Sn, Zn, Co, Mn and Fe. As shown in the following examples, the metal utilized in either the cationic porphyrin or the anionic porphyrin does not affect the general four-fold morphology resulting from the self-assembly of the cationic porphyrin with the anionic porphyrin. The metals in each of the porphyrins can even be the same.

Figure 2:
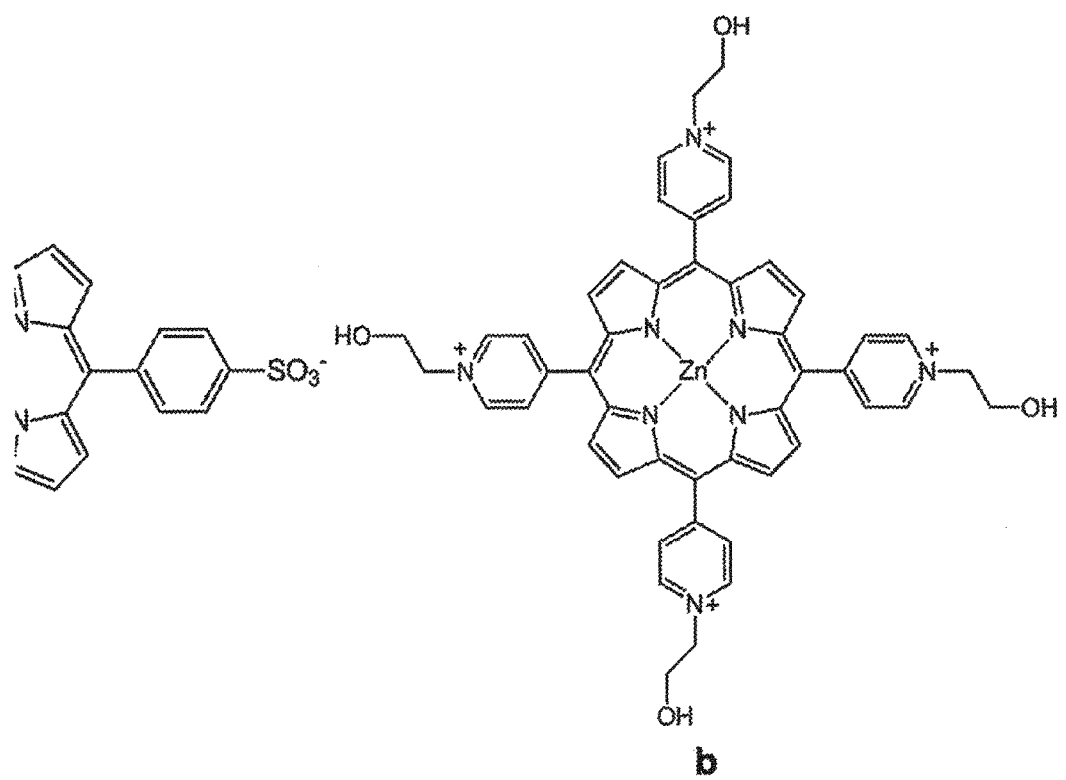
FIG. 2 shows a cationic porphyrin and an anion porphyrin according to the present invention.
Figure 3:
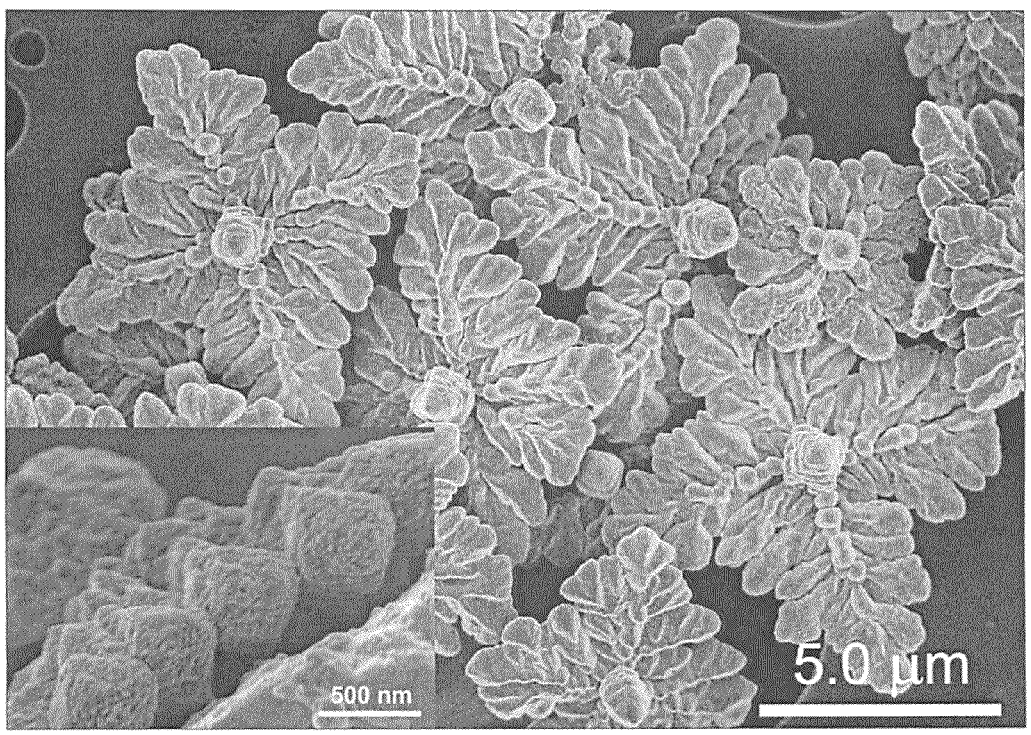
FIG. 3 shows one embodiment of the nanostructure of the molecular unit of the present invention.

Experimentation determined that the substituent of each of the porphyrins is important in the morphology of the resulting nanostructure. When the cationic porphyrin and anionic porphyrin shown in FIG. 2 are mixed and self-assembly occurs, the nanostructure of FIG. 3 is formed with a morphology comprising four dendritic elements connected at central node. However, when the substituent group of the anionic porphyrin is replaced by a carboxylate group, the four-fold morphology is not formed and a fractal or different morphology results. When the substituent group of the cationic porphyrin is replaced by the closely related methyl-4-pyridinium group, again a different or fractal morphology is obtained.

Figure 4:
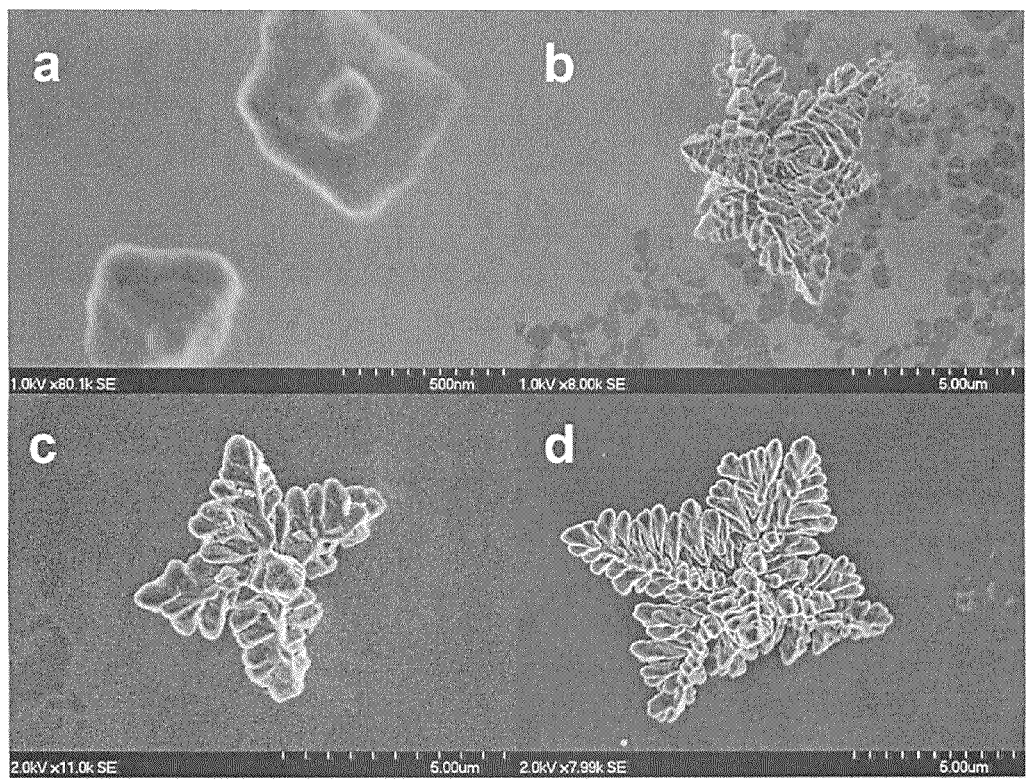
FIG. 4 shows SEM images of the clover-like structures after different reaction times.

In one embodiment, the cationic porphyrin zinc(II) tetrakis (N-ethanol-4-pyridinium)porphyrin is mixed with the anionic porphyrin tin(IV) tetrakis(4-sulfonatophenyl)porphyrin at approximately room temperature and allowed to sit. The self-assembled porphyrin structures of the present invention form quickly after mixing the anionic porphyrin and the cationic porphyrin. FIG. 4 shows SEM images of the clover-like structures after different reaction times. FIG. 4 shows the nanostructure morphology obtained by scanning electron microscopy (SEM) at times of 30 seconds (FIG. 4a), 5 minutes (FIG. 4b), 30 minutes (FIG. 4c) and 2 hours (FIG. 4d). The images show that the clover-like morphology is already established after only 30 seconds. A square morphology is present with raised areas that indicate nascent stems and mid-ribs with nascent square clover-like structures as large as 500 nm on an edge. Mature structures are observed after only 5 minutes. After 30 minutes, the four-fold symmetry is apparent and after two hours, the four dendritic elements connected at a central node are readily observed. This finding is consistent with rapid growth by diffusion limited aggregation from a supersaturated solution leading to these clover-like dendrites. In agreement with this interpretation, cloudiness of the solution is observed immediately after mixing the porphyrin solutions and the solubility of the clovers is very low (<500 nM).

Figure 5:
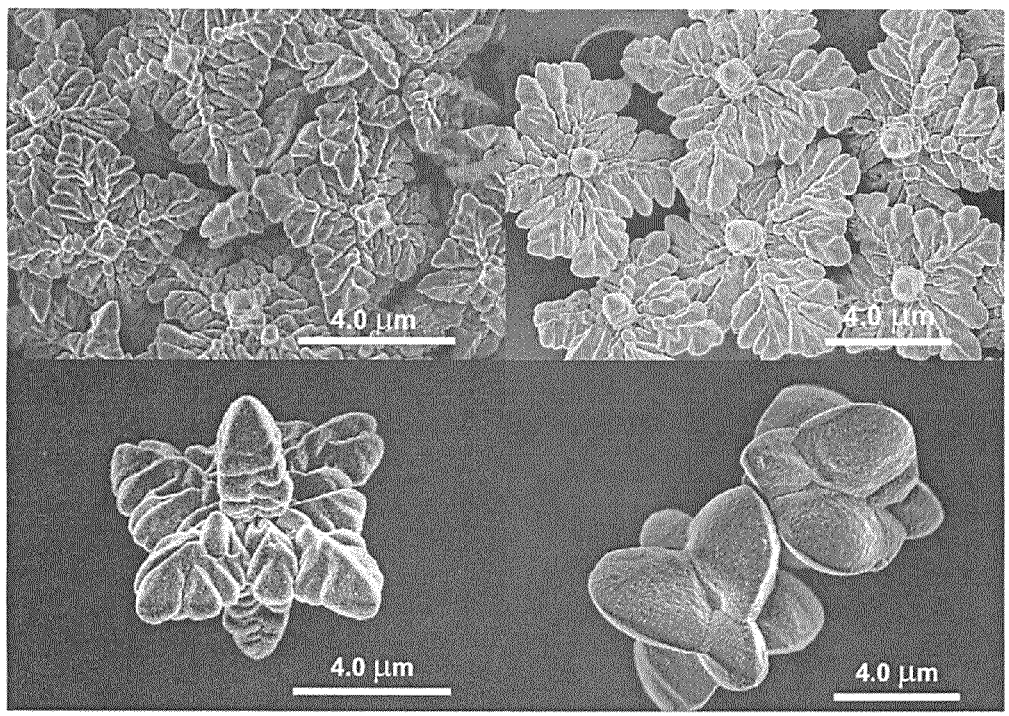
FIG. 5 shows SEM images of porphyrin structures at temperatures from 10° C. up to 80° C.

The temperature at which the cationic and anionic porphyrins are mixed and reacted has a strong influence on the resulting morphology. FIG. 5 shows SEM images of porphyrin structures at temperatures from 10° C. up to 80° C. The SEM images show that multi-fold dendritic structures form throughout this temperature range but that the four-fold dendritic structures as exemplified in FIG. 3 do not form at the higher temperature range. Notice that the structures retain the basic four-fold symmetry of the clovers but have less pronounced nanoscale features as the growth temperature is increased, until at 80° C., the structures have transformed into a smooth and pod-like shape. Just as for high ionic strength, high temperature could be influencing the diffusion-limited self-assembly of these dendritic structures, changing the morphology and causing greater diversity in the structures at 60 and 80° C.

In one embodiment, zinc(II) or tin(IV) were chosen as metals for the porphyrins as these give electron donor or acceptor porphyrin macrocycles. Self-assembly of tin(IV) tetrakis(4-sulfonatophenyl)porphyrin (SnTPPS$^{4-}$) and zinc (II) tetrakis(N-ethanol-4-pyridinium)porphyrin (ZnT(N-EtOH-4-Py)P$^{4+}$), as shown in FIG. 3 produced a dark green precipitate. Scanning electron microscope (SEM) images of the material (see FIG. 3) reveal remarkable 'four-leaf clover'-like structures, with four dendritic elements connected at a central node. The clovers are approximately square with average edge lengths ranging from 2.0 to 10.0 m (as determined by measuring randomly selected clovers from several images and preparations). The clovers are a few hundred nanometers thick as determined from SEM images of clovers trapped edge on to the electron beam (see FIG. 3, inset). Four dendritic elements (i.e., leaves) with well-defined 'veins' (especially the midrib vein) are readily apparent, as well as a central node (i.e., stem or stalk). Complex nanoscale features are visible in high magnification images. This is a striking example of a porphyrin-related biomorph. The most closely related biomorphic structure previously observed is the nano-flower structure obtained by vapor deposition of a phthalocyanine. There are no previously reported biomorphs from a binary porphyrin solid, as obtained in the present invention. Analysis of the supernatant remaining after the synthesis of the structures of FIG. 3 shows that they are composed of SnTPPS$^{4-}$ and ZnT(N-EtOH-4-Py)P$^{4+}$ in approximately a 1:1 molecular ratio. This is expected for an ionic solid for which the self-assembly process is dominated by electrostatic interactions between porphyrin ions which have equal but opposite charges.

Figure 6:
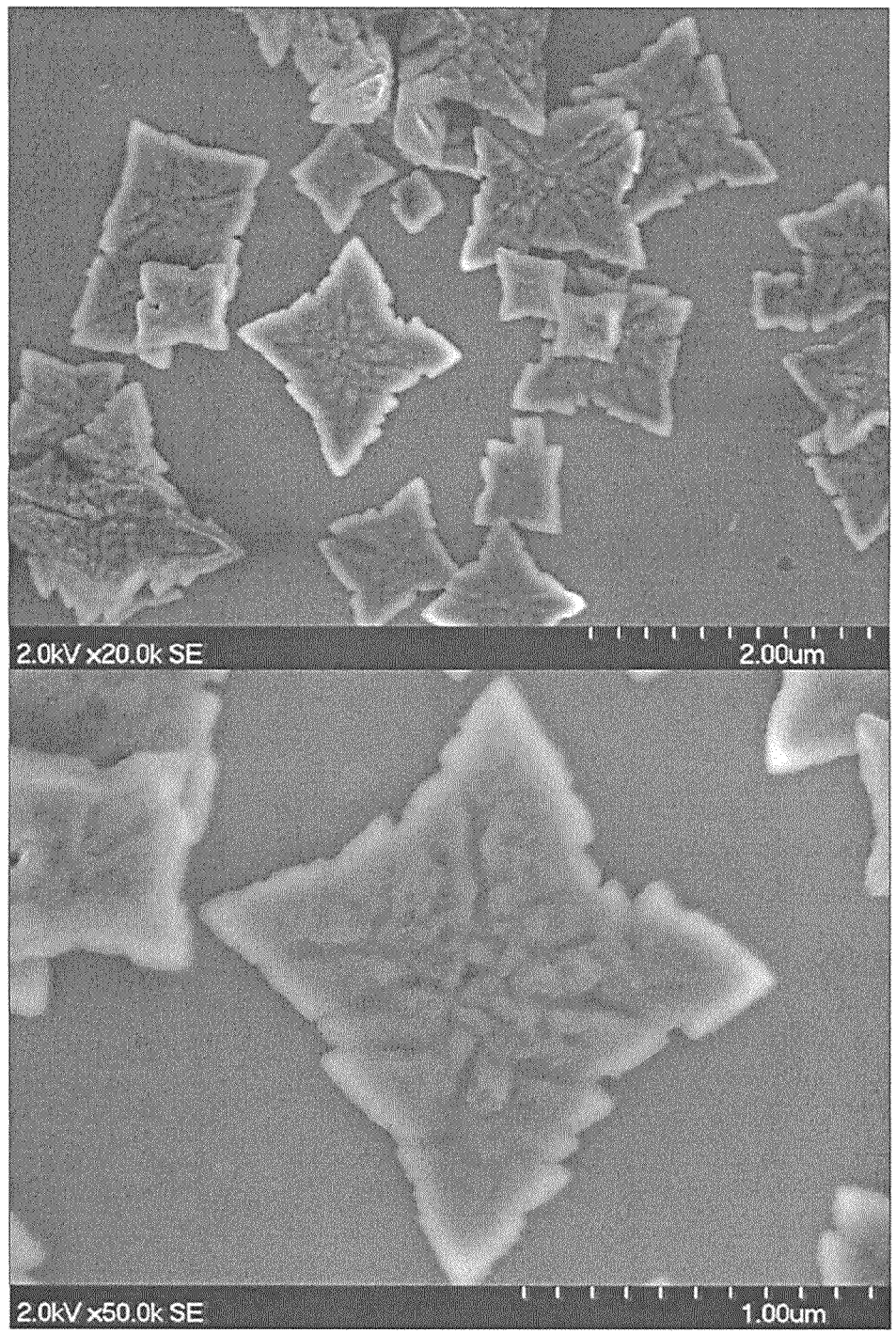
FIG. 6 shows the nanostructure of the molecular unit produced from $ZnTPPS^{4-}$ and $Co(III)T(N-EtOH-4-Py)P^{4+}$.

In another embodiment, the clover-like structures shown in FIG. 6 were produced from ZnTPPS$^{4-}$ and Co(III)T(N-EtOH-4-Py)P$^{4+}$, which combines a Zn porphyrin electron donor and a Co-porphyrin catalyst for CO$_2$ reduction to produce a nanostructure potentially capable of photoassisted CO$_2$ conversion to CO.

Figure 7:
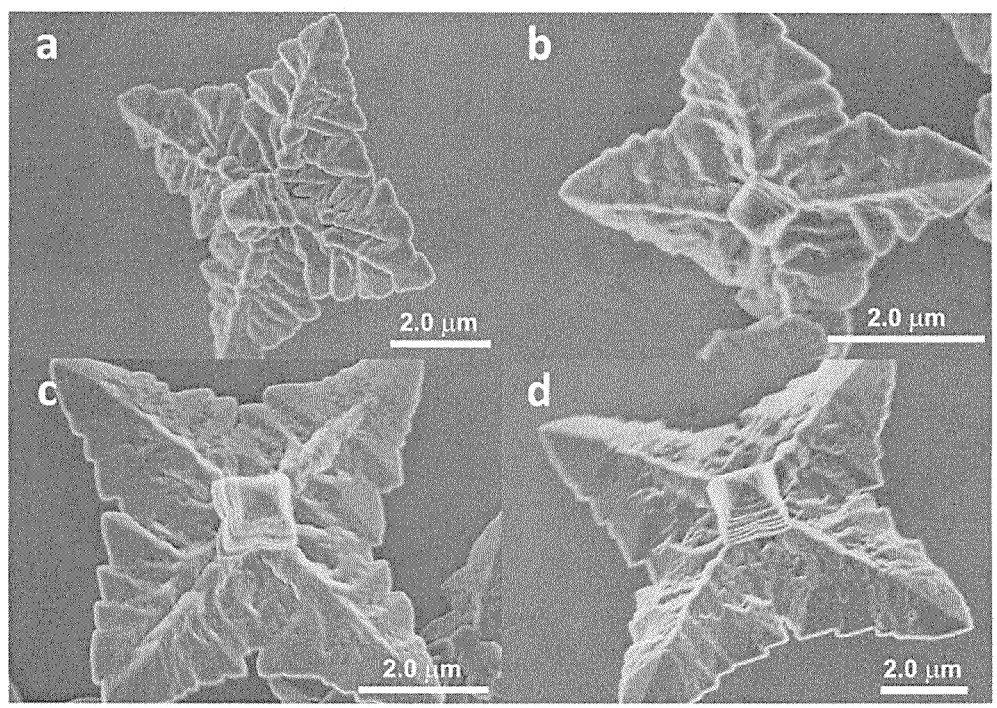
FIG. 7 shows SEM images of nanostructures of the present invention with differing concentrations of added NaCl.

There is no evidence from EDX or ICP-MS that significant amounts of small counter-ions (e.g., Na* or Cl$^-$) are contained in the solid, but the SEM images in FIG. 7 show that ionic strength does influence the morphology of the clovers in FIG. 3 when NaCl is added. Specifically, the complex four-leaf clover motif is maintained as a nanostructure with four dendritic elements connected at a central node but the dendritic elements are more pointed and smooth at the highest salt concentration (20 mM), yielding a star-like appearance. The salt dependence of the morphology might be explained by a variation in the diffusion-limited rate of growth. Increasing the ionic strength shields the charged groups on the anionic and cationic porphyrins, likely slowing the ionic self-assembly process. Also noted is an increase in the diversity of morphologies obtained as the salt concentration increases.

Figure 8:
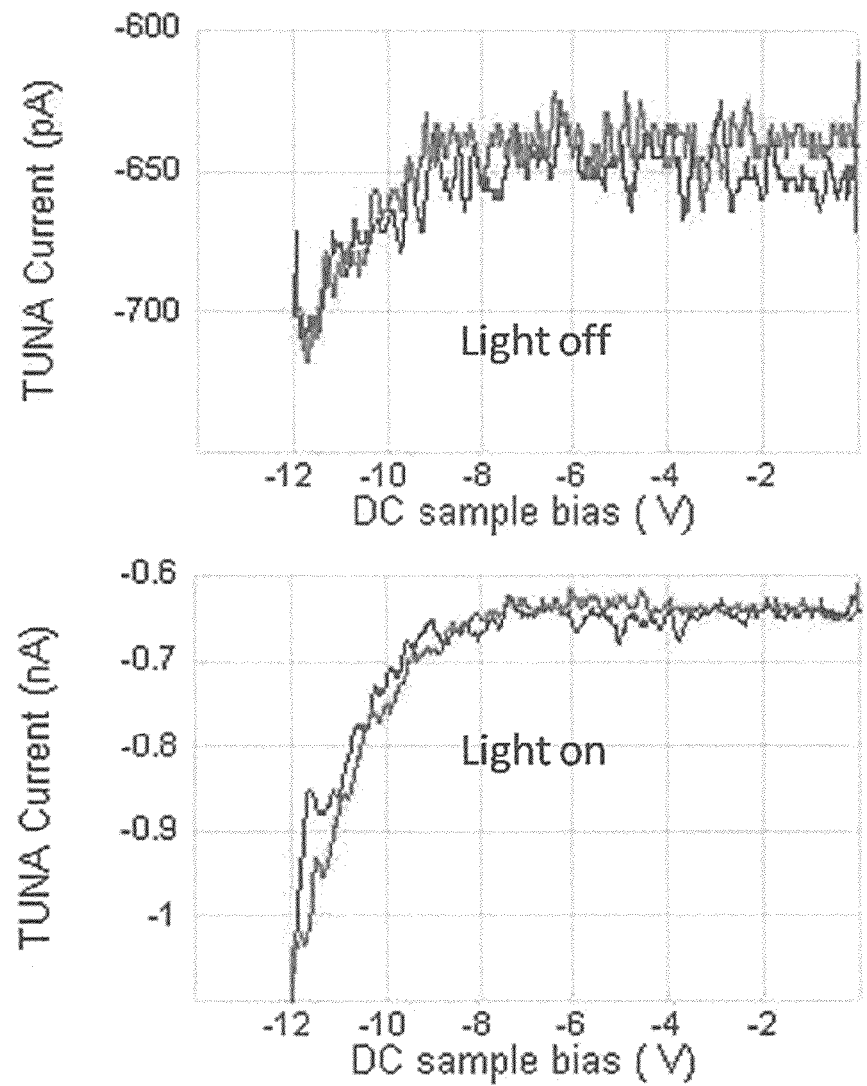
FIG. 8 shows current-voltage curves.

Similar clover-like structures of the same general shape and size of the structures of FIG. 3 are obtained when switching the metals in the two porphyrins; that is, using ZnTPPS$^{4-}$ and SnT(N-EtOH-4-Py)P$^{4+}$. Furthermore, clover-like structures are even obtained when either both tectons are tin porphyrins or both are zinc porphyrins. This is consistent with intermolecular interactions arising from the metals in the porphyrins playing only a minor role, so that clover-like structures are produced regardless of the metals contained in the porphyrins. Although there are minor structural differences when using different metal and substituent combinations, the strong similarities in the dendritic features and basic 4-fold symmetry suggest that they might all share a common molecular packing structure. The morphological similarities suggest the possibility of making binary solids with tunable functional characteristics by selecting appropriate metals, and thus properties, for the two porphyrins. The clover biomorphs are composed of equal proportions of donor molecules (Zn porphyrins) and acceptor molecules (Sn porphyrins), and such donor-acceptor solids often possess interesting electronic properties. Indeed, it was found that the ZnTPPS$^4$/SnT(N-EtOH-4-Py)P$^{4+}$ clovers are photoconductive as shown by conductive AFM studies. In one embodiment, the ZnTPPS$^{4-}$ and SnT(N-EtOH-4-Py)P$^{4+}$ porphyrins were self-assembled and deposited on a p-doped conductive Si substrate. The tunneling currents through the clover nanostructure to a point on the top surface, in the absence and presence of illumination by visible light, are shown in FIGS. 8a and b. A more than 5-fold increase in current between the substrate and tip is observed upon illumination of the clover nanostructure.

Sn(IV) porphyrins are considered acceptors and Zn(II) porphyrins are considered donors because of their respective redox potentials. For both the ground state and (triplet) excited states, the potentials for related redox processes are almost 1.0 volt more negative for Zn(II) than for Sn(IV) porphyrins, making Zn porphyrins the donors and Sn porphyrins the acceptors. The excited state of the Zn porphyrin can easily reduce the Sn porphyrin in either its ground or excited state, moving an electron to an adjacent Sn porphyrin and leaving a hole on the Zn porphyrin. The electron and hole can stay bound, but having the hole and electron on different molecules increases the probability of free charge-carrier formation. The reduction of the Sn porphyrin in its excited state by the ground-state Zn porphyrin is also possible and leads to a similar charge-transfer species. Whether photoconductivity is observed in a donor-acceptor solid such as TTF-TCNQ (tetrathiafulvalene-tetracyanoquinodimethane) usually depends upon the packing mode of the donor and acceptor molecules. The two types of packing that can occur can be generalized as segregated stacking, which leads to electrical conductors and photoconductors, and interleaved stacking, which generally yields insulators. Materials like the clovers are quite different from other donor-acceptor solids as they possess a structure that is not determined by the donor-acceptor interaction but by ionic and other interactions. This provides many possibilities for manipulating the electronic properties by altering interactions between the donor and acceptor molecules, for example by changing the porphyrin substituents to modify the distances between the donor and acceptor macrocycles. Altered interaction between donor and acceptor sometimes leads to enhanced properties. As an example, recently it was shown that pure crystals of TTF and TCNQ (which are individually insulators) could be pressed together to create an interfacial region that is metallic and conducts by a different mechanism than TTF-TCNQ bulk crystals.

The photoconductivity observed for the ZnTPPS$^{4+}$/SnT(N-EtOH-4-Py)P$^{4+}$ clovers and the presence of J-aggregate bands in the UV-visible absorption spectra of this material suggest the presence of a segregated stacking structure. If the porphyrin biomorphs and related materials do exhibit segregated stacking, it is noteworthy that electrostatic channels would be formed in the materials due to the ionic substituents at the corners of the porphyrin squares. For example, in the ZnTPPS$^-$/SnT(N-EtOH-4-Py)P$^{4+}$ clover-like nanostructures, the electrons would presumably end up on the Sn porphyrins and would then see channels lined by the positive charges of the pyridinium groups. Conversely, the holes remaining on the Zn porphyrin would be in channels formed by the negative charges of the sulfonate groups.

EXAMPLES

Example 1

Synthesis of the Molecular Unit Nanostructures

Zn(II)TPPS$^{4-}$, Sn(IV)TPPS$^{4-}$, and Sn(IV)T(N-EtOH-4-Py)P$^{4+}$ were obtained from available suppliers and prepared as stock solutions at a concentration of approximately 210 μM. Zn(II)T(N-EtOH-4-Py)P$^{4+}$ was prepared by dissolving H$_2$T(N-EtOH-4-Py)P$^{4+}$ (58 mg) in methanol (5 ml), adding Zn(OAc)$_2$ (29 mg) and stirring the solution for 1 hr. Chloroform (90 ml) was then added and a stream of air passed over the solution until a green film developed on the surface. The film was removed using a pipette and dried under vacuum for 24 hrs. The purity of the porphyrins was confirmed by proton NMR spectroscopy of D$_2$O solutions. Stock solutions of the porphyrins (210 μM) were prepared in NANOpure™ water and used in the self-assembly reactions. In a typical self-assembly reaction, 10 mL aliquots of stock solutions were added to a 20 mL glass vial, mixed by shaking for 30 seconds, and left undisturbed and shielded from light for 2 days. The clovers were obtained as a dark green precipitate at the bottom of the glass vial. In one embodiment, Zn(II)T(N-EtOH-4-Py)P$^{4+}$ was mixed with Sn(IV)TPPS$^{4-}$ to result in the clover-like nanostructure with four dendritic elements connected at a central node, as shown in FIG. 2. In another embodiment, Zn(II)TPPS$^{4-}$ was mixed with Sn(IV)T(N-EtOH-4-Py)P$^{4+}$ to result in a similar nanostructure with four dendritic elements connected at a central node. In another embodiment using the same metal in both the cationic and anionic porphyrins, Sn(IV)TPPS$^{4-}$ was mixed with Sn(IV)T(N-EtOH-4-Py)P$^{4+}$ to form a nanostructure with four dendritic elements connected at a central node.

Characterization:

Samples for imaging were prepared by pipetting 50 μL of the precipitate layer onto Si wafers (for use in scanning electron microscopy or SEM) or n-type Si wafers (for use in atomic force microscopy or AFM). Excess solvent was wicked away after 10 minutes using a Kimwipe® tissue and the wafer air dried. SEM imaging was performed on a Hitachi S-5200 Nano Scanning Electron Microscope operating at 1-2 keV. AFM measurements were carried out on a Nanoscope III Multimode AFM (Digital Instruments, USA) in contact mode using Si cantilevers.

Salt-, Temperature- and Time-Dependence Studies: The self-assembly reaction of ZnT(N-EtOH-4-Py)P$^{4+}$ and SnTPPS$^{4-}$ was repeated using modified versions of the procedure described above. All reactions were carried out by mixing 1 mL aliquots in a 4 mL glass vial. For the salt dependence studies, sodium chloride was added to the 210 μM porphyrin stock solutions to produce salt concentrations of 1, 2, 5, 10, 15, or mM. The saline stock solutions were then added to a 4 mL glass vial, mixed by shaking for 30 seconds, and left undisturbed and shielded from light for 24 hours. For the temperature-dependence studies, 1 mL aliquots were equilibrated at the required temperature (10, 23, 60 or 80° C.) for 1 hour, rapidly mixed, and then returned to the temperature controlled environment for 24 hours (10 or 23° C.) or 4 hours (60 or 80° C.). In the time-dependence study, aliquots of the stock solutions were mixed by shaking the vial for 5 seconds, and 50 μL portions removed and placed onto Si wafers after 0.5, 5, 10, 20, 30, 60, and 120 mins. The excess liquid was immediately wicked away, the wafer washed with two drops of NANOpure™ water, excess liquid again removed, and the wafer allowed to air dry.

Although the invention has been described with reference to one or more particular embodiments, this description is not meant to be construed in a limiting sense. Various modifications of the disclosed embodiments as well as alternative embodiments of the invention will become apparent to persons skilled in the art. It is therefore contemplated that the appended claims will cover any such modification or embodiments that fall within the scope of the invention. The entire disclosures of all references, applications, patents and publications cited above are hereby incorporated by reference.

We claim:

1. A method for forming a nanostructured molecular unit, comprising:
    mixing at least one cationic porphyrin in a first solvent, said cationic porphyrin comprising ethanolic substituent species, and at least one anionic porphyrin in a second solvent, said anionic porphyrin comprising sulfonate substituent species, forming by self-assembly a nanostructured molecular unit with a morphology comprising four dendritic elements connected at a central node;
    wherein the at least one cationic porphyrin is selected from a group consisting of zinc(II) tetrakis(N-ethanol-4-pyridinium)porphyrin, cobalt (III) tetrakis(N-ethanol-4-pyridinium)porphyrin, and tin(IV) tetrakis(N-ethanol-4-pyridinium)porphyrin; and wherein the at least one anionic porphyrin is selected from a group consisting of tin(IV) tetrakis(4-sulfonatophenyl)porphyrin and zinc(II) tetrakis(4-sulfonatophenyl)porphyrin.

2. The method of claim 1, wherein said at least one cationic porphyrin in a first solvent is at a concentration great than 10 micromolar.

3. The method of claim 1, wherein said at least one anionic porphyrin in a first solvent is at a concentration great than 10 micromolar.

4. The method of claim 1, wherein said nanostructured molecular unit forms after 30 seconds.

5. The method of claim 1, wherein said nanostructured molecular unit forms at temperatures less than 80° C.

6. The method of claim 1, wherein said at least one cationic porphyrin and said at least one anionic porphyrin are self-assembled on a conductive substrate.

7. The method of claim 1, wherein a salt was added to said at least one cationic porphyrin in a first solvent.

8. The method of claim 1, wherein a salt was added to said at least one anionic porphyrin in a second solvent.

9. The method of claim 1 wherein said dendritic element has a side length of greater than 1 micrometer.

* * * * *